(12) United States Patent  
Rinderknecht et al.

(10) Patent No.: US 8,945,448 B2  
(45) Date of Patent: Feb. 3, 2015

(54) METHOD OF MANUFACTURING AN IMPLANTABLE DRUG DELIVERY SYSTEM INCLUDING AN IMPEDANCE PUMP

(75) Inventors: Derek Rinderknecht, Arcadia, CA (US); Hasham Azizgolshani, Winnetka, CA (US); Mortez Gharib, Altadena, CA (US)

(73) Assignee: California Institute of Technology, Pasadena, CA (US)

( * ) Notice: Subject to any disclaimer, the term of this patent is extended or adjusted under 35 U.S.C. 154(b) by 0 days.

(21) Appl. No.: 13/491,385

(22) Filed: Jun. 7, 2012

(65) Prior Publication Data

US 2013/0041319 A1    Feb. 14, 2013

Related U.S. Application Data

(60) Provisional application No. 61/494,317, filed on Jun. 7, 2011, provisional application No. 61/562,957, filed on Nov. 22, 2011.

(51) Int. Cl.
     *B29C 39/10*      (2006.01)
     *B29C 39/12*      (2006.01)

(52) U.S. Cl.
     USPC ............ 264/248; 264/250; 264/263; 264/255

(58) Field of Classification Search
     None
     See application file for complete search history.

(56) References Cited

U.S. PATENT DOCUMENTS

| | | | |
|---|---|---|---|
| 5,833,915 A * | 11/1998 | Shah | 264/491 |
| 6,254,355 B1 | 7/2001 | Gharib | |
| 6,679,687 B2 | 1/2004 | Gharib | |
| 7,153,325 B2 | 12/2006 | Kim et al. | |
| 7,163,385 B2 | 1/2007 | Gharib et al. | |
| 7,387,500 B2 | 6/2008 | Gharib | |
| 2005/0074340 A1 * | 4/2005 | Xu et al. | 417/395 |
| 2007/0043335 A1 | 2/2007 | Olsen et al. | |
| 2007/0085449 A1 | 4/2007 | Boey et al. | |
| 2007/0122299 A1 * | 5/2007 | Wen et al. | 417/413.2 |
| 2007/0177997 A1 | 8/2007 | Gharib et al. | |
| 2009/0209945 A1 * | 8/2009 | Lobl et al. | 604/891.1 |
| 2010/0305551 A1 * | 12/2010 | Lobl et al. | 604/891.1 |
| 2011/0125136 A1 * | 5/2011 | Gharib et al. | 604/890.1 |
| 2012/0015428 A1 * | 1/2012 | Seale et al. | 435/283.1 |

FOREIGN PATENT DOCUMENTS

WO    WO2009/092067 A2    7/2009

OTHER PUBLICATIONS

PCT/US2012/041418, US, Written Opinion, Jan. 29, 2013.

* cited by examiner

*Primary Examiner* — Edmund H. Lee
(74) *Attorney, Agent, or Firm* — One LLP

(57) ABSTRACT

Described herein are systems, devices, and methods for the delivery of substances to, or the sampling of substances from, a patient using a portable and preferably implantable device. The substances introduced to and/or taken from the patient are preferably fluidic and are driven by a miniature pump, such as a microimpedance pump. A number of design variations are explicitly and implicitly described, such as the use of multiple pumps and multiple reservoirs for containing medicaments. Methods of manufacture of these systems and devices are also described, for instance, using molding, micromachining, or lithographic processes.

5 Claims, 5 Drawing Sheets

METHOD OF MANUFACTURING AN IMPLANTABLE DRUG DELIVERY SYSTEM INCLUDING AN IMPEDANCE PUMP

CROSS REFERENCE TO RELATED APPLICATIONS

The present application claims the benefit of U.S. provisional patent application Ser. No. 61/494,317 filed Jun. 7, 2011 and U.S. provisional patent application Ser. No. 61/562,957 filed Nov. 22, 2011, both of which are hereby incorporated by reference in their entirety as if fully set forth herein.

RELEVANT FIELD

The systems and methods disclosed herein relate generally to portable drug delivery and sampling devices having impedance pumps.

BACKGROUND

For many diseases, treatment with oral or parenteral medicament administration requires a high dose which would lead to side effects that would inhibit a therapeutic concentration of the medicament from reaching diseased tissue. Thus, for such diseases, local medicament delivery to the diseased tissue is a desirable objective. It can provide higher concentrations of the medicament to the diseased tissue and allow control of the amount, rate and timing of delivery, which makes local delivery an option for long-term continuous treatment and potentially reduces systemic side effects. However, for some anatomical structures, such as the inner ear, local medicament delivery has special challenges due to, for example, limited natural points of entry, complex structures, barriers, and delicate environments. Known delivery modalities, e.g., systemic, intratympanic, etc., have not adequately or effectively addressed these challenges. Therefore, there is a need for a medicament delivery system that can provide localized delivery of a medicament.

SUMMARY

Described herein are systems, devices, and methods for the delivery of substances to, or the sampling of substances from, a patient using a portable and preferably implantable device. The substances introduced to and/or taken from the patient are preferably fluidic and are driven by a miniature pump, such as a microimpedance pump. A number of design variations are explicitly and implicitly described, such as the use of multiple pumps and multiple reservoirs for containing medicaments. Methods of manufacture of these systems and devices are also described, for instance, using molding, micromachining, or lithographic processes.

Other systems, methods, features and advantages of the subject matter described herein will be or will become apparent to one with skill in the art upon examination of the following figures and detailed description. It is intended that all such additional systems, methods, features and advantages be included within this description, be within the scope of the subject matter described herein, and be protected by the accompanying claims. In no way should the features of the example embodiments in this summary section, or in the following description sections, be construed as limiting the appended claims, absent express recitation of those features in the claims.

BRIEF DESCRIPTION OF FIGURES

The details of the systems, devices, and methods described herein, both as to their structure and operation, can be gleaned in part by study of the accompanying figures, in which like reference numerals refer to like parts. The components in the figures are not necessarily to scale, emphasis instead being placed upon illustrating principles. Moreover, all illustrations are intended to convey concepts, where relative sizes, shapes and other detailed attributes may be illustrated schematically rather than literally or precisely.

DETAILED DESCRIPTION

The detailed description set forth below in connection with the appended drawings is intended to describe various example embodiments and is not intended to represent the only embodiments that may be practiced.

In the following section, numerous examples and example embodiments are described. These embodiments are not described as rigid alternatives, but are rather intended to illustrate the broad scope and interchangeability of the systems, devices, and methods described herein. Thus, any feature, element, step, or aspect of one embodiment can be added to or substituted within any other embodiment described herein.

Figure 1:
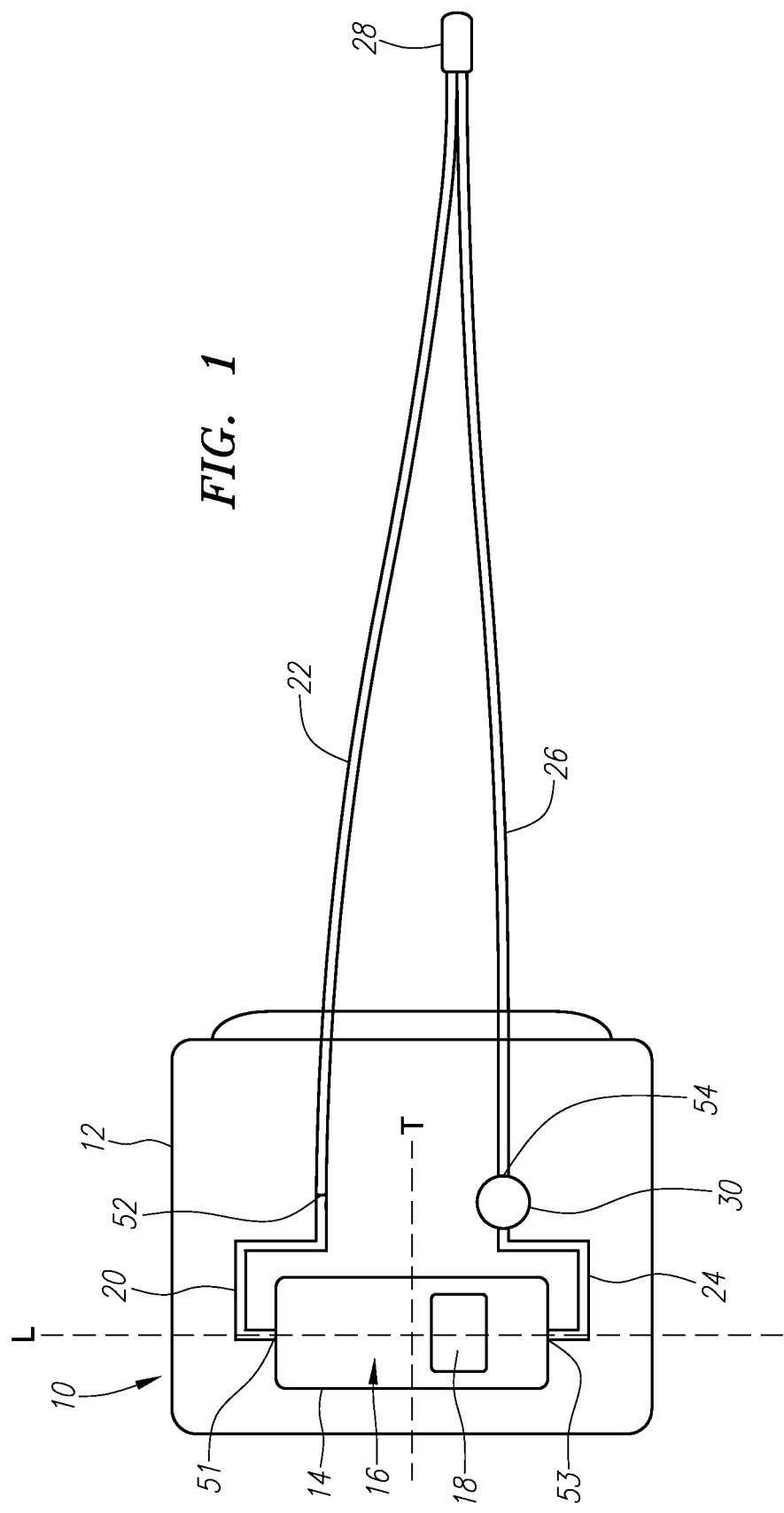
FIG. 1 is a schematic view depicting an example embodiment of a medicament delivery system.

An example embodiment of a medicament delivery system 10 is shown in FIG. 1. Generally, the delivery system 10 is intended to be used to deliver a medicament into the inner ear for the treatment of inner ear and/or vestibular system disorders (e.g., tinnitus, SNHL, presbycusis, meniere's disease, etc.). While the embodiments described herein will be done so generally with regard to inner ear delivery, it should be understood that these embodiments can be used to deliver substances to any desired tissue or anatomical structure, including but not limited to intrathecal delivery (e.g., for pain management) and intraocular delivery. Likewise, the delivery system can be used to deliver any desired substance, drug, medicament, or therapeutic, including but not limited to cancer therapeutics and insulin.

In the example embodiment of FIG. 1, the delivery system 10 can be implanted in the mastoid portion of the temporal bone. In an example implantation procedure, a pocket can be formed in the mastoid bone for insertion of the delivery system 10. Holes can be drilled to provide access to the scala tympani for the delivery system 10. In another example embodiment, the delivery system 10 can be implanted using a postauricular mastoidomy or posterior tympanotomy. The delivery system 10 can also be configured to lie outside the body and deliver a substance through a catheter or subcutaneously through a needle. Alternatively, the delivery system 10 can lie outside the body and sample body fluids through a catheter or subcutaneously through a needle. In yet another example, the delivery system 10 can lie outside the body and deliver or sample substances through the dermis.

The delivery system 10 includes a substrate (or body) 12, pump 16 and tubing that can be manufactured from biocompatible polymeric materials (including, but not limited to, silicone, PDMS, PEEK, PTFE and Polysulfone (PSU), other fluoropolymers, PVDF, parylene, polyurethane, polysulphone, polyolefin, polyvinyl chloride, polypropylene, polycarbonate, and PMMA), metallic materials (including, but not limited to, nickel, titanium, and any alloys thereof (e.g., Ti6Al4V), stainless steel, and chromium), ceramics (including, but not limited to, zirconia and alumina), or combinations of the same.

In an example embodiment, the substrate 12 can include a pump chamber 14 which houses a pump 16 for circulating fluid through the delivery system 10. Pump 16 preferably utilizes a mismatch in impedance to drive flow and can be embodied by a compressible section or movable wall coupled at either end to wave reflection sites or locations where pressure wave energy is reflected. Here, pump 16 is an impedance pump enclosed within substrate 12. Pump 16 can be manufactured from one or more materials and can assume any desired shape. In this example, pump 16 is made from silicon and is rectangular. In embodiments where pump 16 is manufactured from two or more materials, the first material can have a first impedance and the second material can have a second impedance, different from the first. Of course, any number of materials having different impedances can be used. Further examples of pump 16 can be, but are not limited to, those pump configurations and geometries described in U.S. Pat. Nos. 6,254,355, 6,679,687, 7,387,500, 7,163,385 and U.S. Patent Application Publication Nos. 2007/0177997 and 2011/0125136. Every patent and published application in the preceding sentence is expressly incorporated herein by reference for all purposes.

Here, pump 16 has a longitudinal axis L and a transverse (or lateral) axis T. An activation element 18 (e.g., a magnet) can be disposed on a surface of substrate 12, preferably a surface of a thin wall or membrane opposite pump chamber 14. Activation element 18 is adapted to activate and/or instigate the mechanism that causes the pumping action, which in this embodiment is the movement of the thin wall underlying element 18. Activation element 18 can be a piezoelectric, electromagnetic, or magnetostrictive device, to name a few. Activation element 18 preferably interfaces with a control device, which can also be a portable (e.g., wearable, implantable, or handheld) device located in proximity with delivery system 10. The control device (not shown) can generate a permanent or variable magnetic field that interfaces with, e.g., a magnetic activation element 18 and causes that activation element to move. The control device is preferably programmable and adjustable based on user input. In one example embodiment, the control device has on-board electronics such as power management, frequency synthesizer, controller, communication links, and a battery.

The device 10 itself may be implanted subcutaneously or worn externally with the drug perfusion tubing extending into the patient. In another example embodiment, the device functions as an in hospital delivery platform for drug perfusion through a venous or arterial catheter placed in the patient. In another embodiment device 10 functions in combination with a cochlear implant providing both stimulation and therapeutic treatments.

In the instance where the geometry of the ends of channels 20, 24 leading into pump chamber 14 are the same, then magnet 18 is preferably disposed at a position longitudinally offset from the central transverse axis T of pump chamber 14. This asymmetry leads to the addition of pressure waves within chamber 14 that in turn creates the pumping effect (see, e.g., the incorporated U.S. Pat. No. 7,163,385). The geometry of the ends of channels 20, 24 leading into pump chamber 14 can also be different, sized in the appropriate manner to allow activation element 18 to be centrally placed along axis T.

A first channel 20 is disposed in substrate 12 and has a first opening 51 in fluid communication with pump 16 and a second opening 52 in fluid communication with an inlet tube 22. Here, openings 51 and 52 are also located at opposite terminal ends of channel 20. A second channel 24 is disposed in substrate 12 and has a first opening 53 in fluid communication with pump 16 (at an end of pump 16 opposite opening 51 of first channel 20) and a second opening 54 disposed in fluid communication with an outlet tube 26. Here, openings 53 and 54 are also located at opposite terminal ends of channel 24. First and second channels 20, 24 define a fluid path through substrate 12 for fluid being pumped by the pump 16. The cross-sectional area of the channels 20, 24 can be the same or different from each other, but in either case are substantially less than the transverse cross-sectional area of pump 16.

Delivery system 10 can be used with multiple pumps. These additional pumps can be used to deliver different drugs (e.g., to allow the delivery of drug combinations or drug cocktails), or used in a cascaded or additive configuration (e.g., to increase the flow rate of the pumping mechanism with system 10). In another embodiment, one or more pumps are used to draw fluid out of a liquid reservoir to combine drugs or drug components. In another embodiment, delivery system 10 contains a mixer utilizing an unsteady output of a pump to combine drugs or drug components.

Although the term "delivery system" is used, it should be noted that in all of the embodiments described herein, the pump can be used with the primary intent to deliver a foreign substance into the patient, or with the primary intent to extract a substance from the patient (such as blood for diagnostic purposes). In embodiments where a fluid circuit is used to both pass a substance into the patient and extract a substance from the patient, those of skill in the art will readily recognize that the pump accomplishes both a delivery and extraction function. In FIG. 1, a single pump 16 accomplishes both functions, but system 10 can be configured with dedicated pumps where one or more pumps primarily (or exclusively) deliver a substance to the body and one or more different pumps primarily (or exclusively) extract a substance from the body.

Drug perfusion tubing in the form of inlet and outlet tubes 22, 26 can extend laterally from substrate 12 with terminal ends coupled in proximity to each other or coupled to an interface component 28 (e.g., a connector). For instance, the terminal ends of the tubes 22, 26 on the patient-side can be configured or molded as a single dual lumen tube. Interface component 28 can be implanted into the inner ear (e.g., via a cochleostomy), allowing perilymph to circulate through tubes 22 and 26, channels 20 and 24, and pump 16. Interface component 28 can also be secured to the scala tympani with an adhesive or a graft. While tubes 22, 26 are described as "inlet" and "outlet" tubes in the example embodiment, those of skill in the art will understand that such terminology is for reference only, and that each tube can act as an inlet or an outlet depending on the direction of circulation of fluid through delivery system 10. Tubes 22, 26 can be manufactured from any desired metal, metallic alloy, or polymeric material (e.g., PEEK). One or more sheaths (not shown) can be used to cover each of tubes 22, 26, for example, to prevent kinking of tubes 22, 26 or accommodate potential displacement of delivery system 10 within the mastoid bone. One sheath can cover both tubes 22, 26 or separate sheaths can cover each tube 22, 26 alone.

A sensor (not shown) can also be included along inlet tube 22 or first channel 52 and used to analyze the fluid sampled by the system 10. Alternatively (or additionally), the sensor (or the fluid being delivered by system 10).

In an example embodiment, one or more reservoirs 30 are formed in substrate 12 for containing a substance, e.g., a medicament, a diagnostic agent, etc. Reservoir 30 can be in fluid communication with first channel 20 and/or second channel 24 such that the fluid circulating through delivery system 10 contacts the medicament contained in reservoir 30. Reservoir 30 can be in fluid communication with first channel 20 and/or second channel 24 such that fluid does not circulate through delivery system 10 yet contacts the medicament contained in reservoir 30. A plurality of reservoirs 30 can be in disposed in substrate 12. In such embodiments, reservoirs 30 can be disposed in series or parallel along a channel. Examples of such arrangements are described in the incorporated U.S. Patent Application Publication 2011/0125136.

Figure 4A:
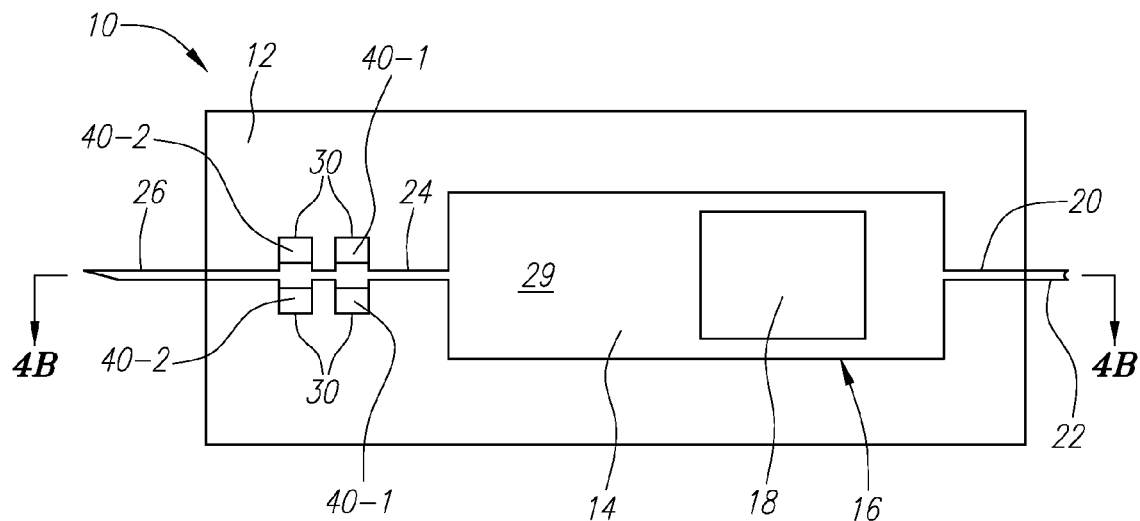
FIGS. 4A-B depict another example embodiment of a medicament delivery system.
Figure 4B:
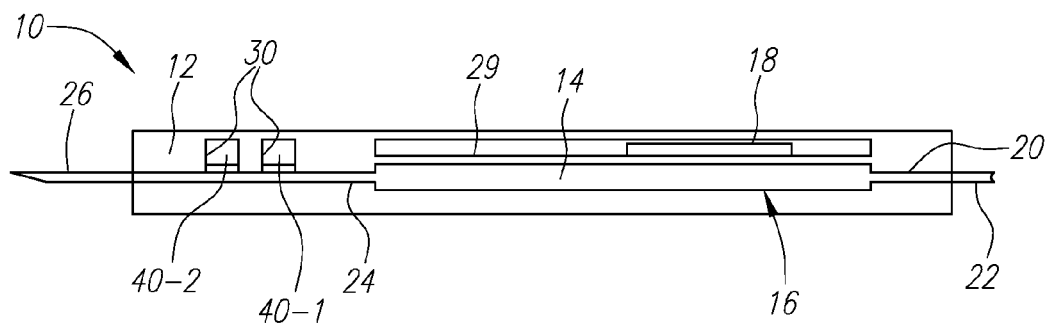

FIG. 4A is a top down view of another example embodiment of delivery system 10 where multiple reservoirs 30 are present. FIG. 4B is a cross-sectional view taken along line 4B-4B of FIG. 4A. Here, four reservoirs are present and immediately adjacent channel 24. Medicament 40 in the form of a solid pill-like element is present within each reservoir 30, where one type of medicament 40-1 is in two reservoirs and another type of medicament 40-2 is in the other two reservoirs. It should be noted that system 10 can be an integrated (or monolithic) device, or can be modular with, for instance, pump 16 in one module and reservoir 30 in a separate connectable module. Such a configuration would allow for easy replacement of the medicament.

Reservoirs 30 can also be piggy-backed on each other, such that pumped fluid will contact a substance in a first reservoir, and that reservoir will empty (or the substance will be exhausted) before fluid contacts the same or a different substance in a second reservoir. In another embodiment, the terminal ends of the tubes 22, 26 are coupled to two separate interface components, for example, to allow outlet tube 26 to be located in the tissue of interest and to allow inlet tube 22 to be coupled to a liquid reservoir containing, e.g., a liquid formulated drug or a carrier fluid for a drug in solid form located in reservoir 30.

The medicament contained in any reservoir 30 can be a solid formulation (e.g., a monolithic pill, particulates, etc.), a gel formulation (with or without a suspension), a liquid formulation, a slurry formulation, and the like. Example medicaments which can be included in the delivery system 10 are nomifensine and dexmethasone. However, those of skill in the art will understand that other medicaments can be utilized depending on the therapeutic purpose of the delivery system 10. A more comprehensive (but non-exhaustive) list is provided in the "Substances and Applications" section.

The medicament is preferably formulated to prevent portions of the medicament from breaking off and occluding any portion of system 10, particularly channels 20, 24 and/or tubes 22, 26. For example, the medicament can be disposed in a polymeric matrix which maintains structural integrity while in contact with the fluid circulating through delivery system 10. A physical safeguard can also be used to prevent partial or complete occlusion. For instance, the medicament can be disposed in a semi-permeable membraneous coating, which can allow for diffusion of the fluid and the dissolved medicament, but prevent large particles of medicament from passing through. Alternatively (or additionally), a molecular sieve can be used as a filter that allows diffusion of the fluid and the dissolved medicament, but prevents large particles of medicament from passing through.

The main body of system having substrate 12 is preferably small enough to be implanted without difficulty. In one example, which is provided for illustrative purposes only and is not intended to be limiting, the dimensions of the main body of system 10 (without the perfusion tubing) is 5 mm by 20 mm by 20 mm, although both smaller and larger sizes are possible. The perfusion tubes each preferably have a diameter of less than 1 mm, although larger sizes can be used. When used to treat diseases of the inner ear, e.g., tinnitus, the preferred depth of implantation into the scala tympani is less than 0.5 mm.

FIGS. 2A-F depict an example embodiment of a manufacturing process for a delivery system 10. This embodiment generally relates to a two layer system, although one of ordinary skill in the art will readily recognize that three or more layers can be used, depending on the complexity of the system, the number of pumps, reservoirs, sampling wells, channels, etc.

Figure 2A:
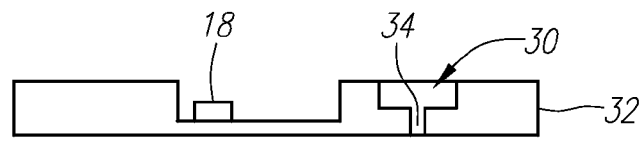
FIGS. 2A-F are cross-sectional views depicting an example method of manufacture of a medicament delivery system.
Figure 2B:
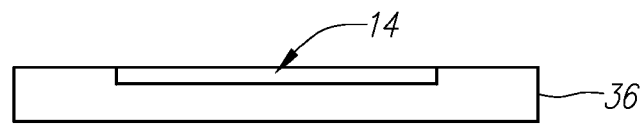

In FIGS. 2A-B, a first layer 32 and a second layer 36 of substrate 12 are provided. Layers 32 and 36 can be formed or molded with the appropriate elements therein. This can be done by first creating a mold with the positive impressions of the elements thereon, such as through micromachining (e.g., soft lithography) or photolithography. Layers 32 and 34 will then be formed with negative impressions of those elements therein. For layer 32, this includes a chamber for magnet 18, reservoir 30, and a vertical channel 34, while for layer 36, this includes the pump chamber 14 (present in this stage as an elongate recess), and first and second elongate channels 20, 24 (not shown). The formation of layers 32, 36 can also be done by micromachining or photolithography to etch or carve the elements directly into layers 32, 36.

Figure 2C:
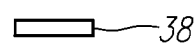

Magnet 18 is coupled to (or seated in) layer 32 after formation the magnet chamber. Afterwards, the magnet chamber can be filled with silicon. Beneath magnet 18 is a thin wall or membrane that can be displaced to generate the pumping forces. As shown in FIG. 2A, a vertical channel 34 is present to create a fluid path to/from reservoir 30. FIG. 2C depicts a reservoir plug 38.

Figure 2D:
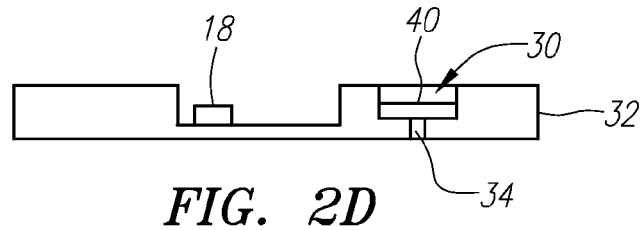
Figure 2E:
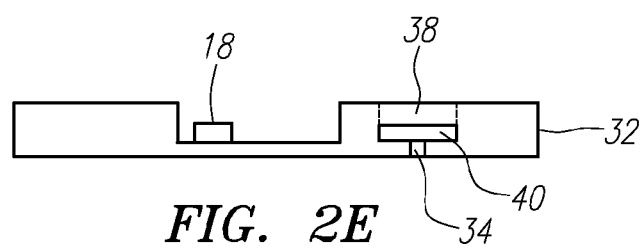

FIG. 2D depicts a medicament 40 disposed in reservoir 30. In this example embodiment, medicament 40 is a solid pellet which sits in reservoir 30 and abuts an open end of vertical channel 34. FIG. 2E shows reservoir plug 38 coupled to first layer 32 to seal medicament 40 in reservoir 30. Plug 38 can be bonded to first layer 32 by plasma treatment, curing of first layer 32, or through the use of an adhesive. In another example embodiment, plug 38 can be molded into first layer 32. In yet another example embodiment, plug 38 can be a resealable septum which covers reservoir 30 but allows for re-filling, e.g., by a needle injecting a medicament into reservoir 30.

Figure 2F:
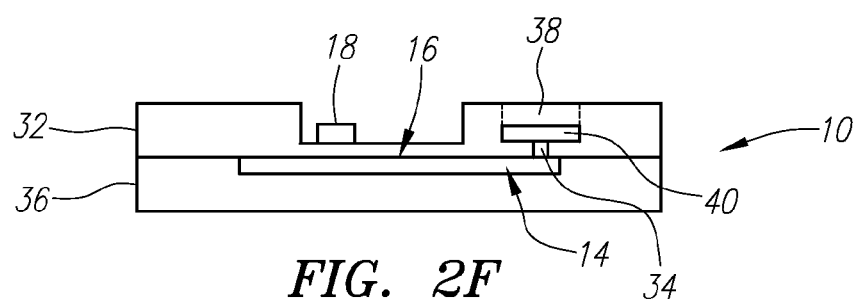

FIG. 2F shows first layer 32 coupled to the second layer 36. First layer 32 forms a cover or roof to second layer 36, enclosing the elongate recess to form pump chamber 14 with the thin pump chamber wall present in layer 32. The elongate channels are also covered to fully enclose them (with the exception of the open ends through which fluid flows). In an example embodiment, layers 32, 36 are bonded by $O_2$ plasma treatment and a subsequent bond curing period in an oven at 80° C. In another example embodiment, layers 32, 36 can be bonded through thermal treatments at 80° C. by adjusting a ratio of a curing agent in a mixture used to fabricate layers 32, 36. In yet another example embodiment, layers 32, 36 are sealed using UV ozone treatment or any other treatment which hydrophilizes the surface of silicone. In yet another example embodiment, layers 32, 36 are bonded using an adhesive, e.g., uncured PDMS. In still another example embodiment, system 10 is hermetically sealed to prevent the intrusion of bodily fluids.

Figure 2G:
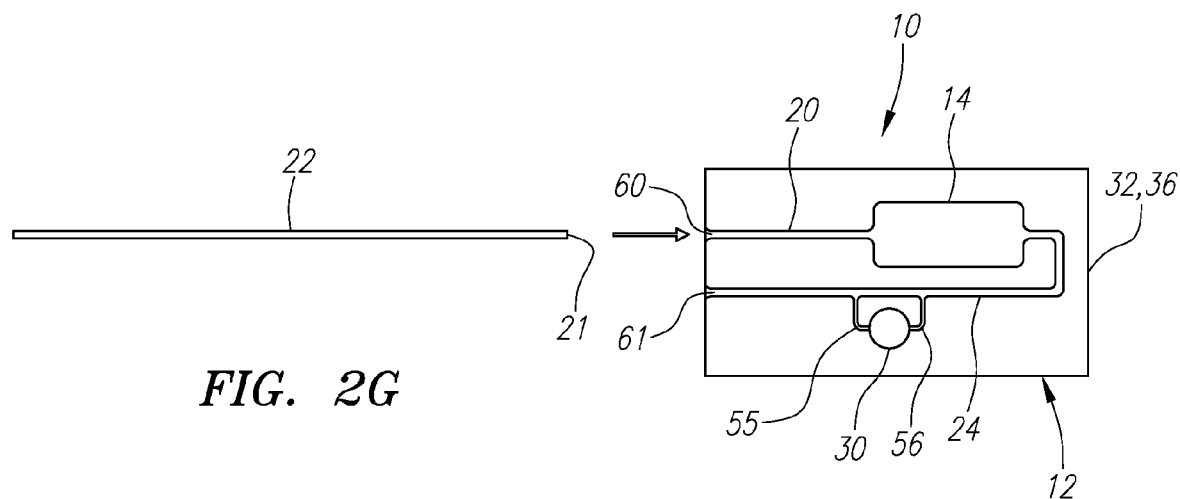
FIGS. 2G-H are schematic views depicting an example method of securing inlet and/or outlet tubes to the delivery system substrate.
Figure 2H:
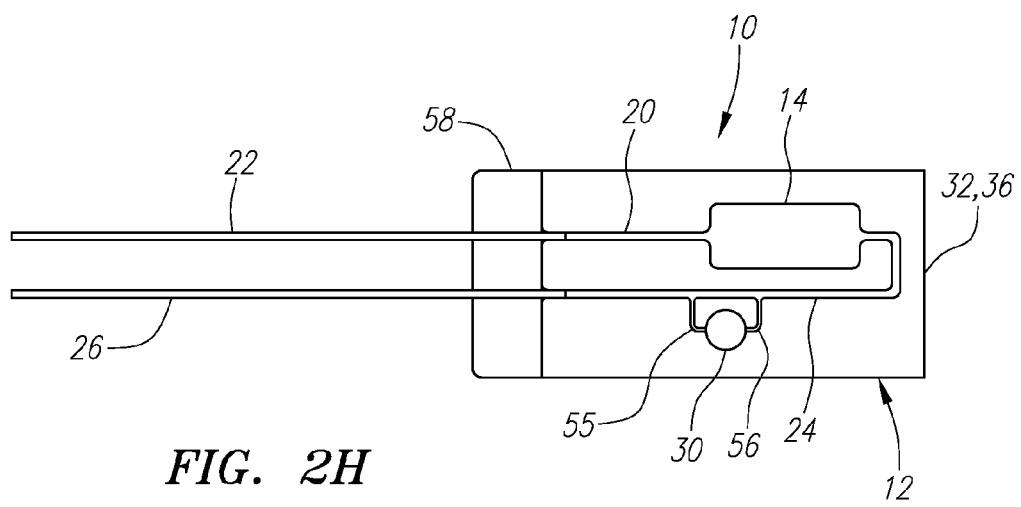

An overmolding process is preferably used to secure the inlet and outlet tubes 22, 26 with respect to channels 20, 24. FIGS. 2G-H depict an example method used in the securement of tubes 22, 26 with respect to substrate 12 for a similar but alternate layout to system 10. In this layout, reservoir 30 is located laterally offset from channel 24 and is coupled to channel 24 by way of two feeder channels 55 and 56, each having a cross-sectional dimension less than channel 24. This layout can allow for less concentrated doses.

Preferably, after first layer 32 is coupled to second layer 36, tubes 22, 26 are press-fit into openings 60, 61 for channels 20, 24, respectively. FIG. 2G shows the press-fitting insertion of tube 22 into opening 60 and along a length of channel 20. An adhesive can be used to further secure the coupling of tubes 22, 24 to substrate 12 after press-fitting.

After both tubes are inserted, an overmolding process can then be used to encapsulate and fully secure tubes 22, 26 to substrate 12. Uncured silicone is poured into a mold holding tubes 22, 26 in the substrate 12 and also holding layers 32, 36 together. A priming solution can be used to increase bond strength between tubes 22, 26 and substrate 12. This assembly can then be baked in an oven (e.g., at 80° C.) and cured. The overmolding process adds an overmolded portion 58 to the length of substrate 12 and surrounds (or encapsulates) and stabilizes tubes 22, 26 and layers 32, 36. The overmolding process can be followed by application of an adhesive to tubes 22, 26 to further secure them to substrate 12. In another example embodiment, tubes 22, 26 are molded into first layer 32 or second layer 36, or one tube is molded into first layer 32 and the other tube is molded into second layer 36.

Figure 3A:
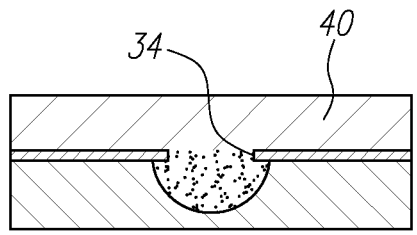
FIGS. 3A-E are cross-sectional views depicting example flow distributions for medicament exiting a medicament delivery system.
Figure 3B:
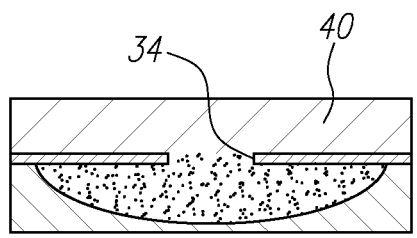

FIGS. 3A-E show an example embodiment of medicament delivery by delivery system 10. In FIG. 3A, fluid (e.g., perilymph) circulating through delivery system 10 contacts medicament 40. For example, as the fluid enters delivery system 10, the fluid can push up through vertical channel 34 and contact medicament 40, which allows medicament 40 to dissolve or disperse into the fluid. As shown in FIG. 3B, prolonged contact between the fluid and medicament 40, such as when pump 16 is inactive, can allow more of medicament 40 to dissolve into the fluid. Delivery system 10 can include valves to restrict flow during periods of pump inactivity. Multiple valves can be used. One or more valves can be placed before or after the pump along channel 20 and/or 24. One or more valves can also be placed between reservoir 30 and channels 20 or 24 (e.g., valves in one or more of feeder channel 55, feeder channel 56, and vertical channel 34). The valves can be off-the-shelf or custom built. The valves can be micro-machined, or fabricated in MEMS, multi-leaflet (e.g., bi-leaflet), check, or pincher-type, to name a few.

Figure 3C:
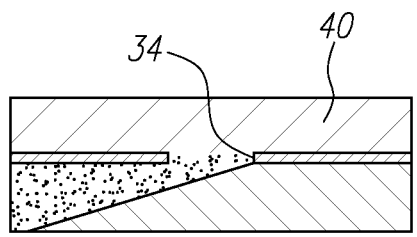
Figure 3D:
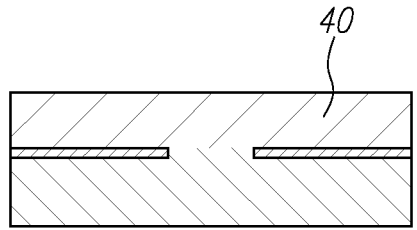
Figure 3E:
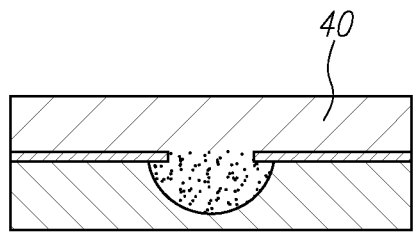

FIG. 3C shows a displacement of the dissolved medicament 40 when pump 16 is activated, e.g., by passing an external actuator (magnet) over magnet 18. When this occurs, magnet 18 on pump 16 moves the wall on which it is mounted and compresses the pump chamber to push fluid through delivery system 10. Vibrational waves travel along pump 16 and bounce off an interface between pump 16 and channels 20, 24, due to the rapid change in surface area between the cross-sectional area of pump chamber 14 and the cross-sectional area of channels 20, 24. Changing location of magnet 18 on axis L of pump 16 and/or changing the frequency of oscillations of pump 16 can increase/decrease, or even reverse direction of, fluid flow. FIG. 3D shows that while pump 16 is activated, the fluid can be pushed past vertical channel 34 and less fluid can contact medicament 40. Thus, when pump 16 is inactive, a "dose" of medicament 40 can be allowed to dissolve into the fluid, as shown in FIG. 3E.

In one example method of delivery, the fluid channels are allowed to fill with the drug and, while the pump remains inactive, the drug spreads diffusely as depicted in FIGS. 3A-B. This can be referred to as mode one. Once the effective dose has been reached, determined either by time or the presence of a sensor, pump 16 is activated and the drug is washed out with the fluid transitioning through the channels, as depicted in FIGS. 3C-D. This can be referred to as mode two. After this the pump is turned off again (or made inactive) as shown in FIG. 3E. The combination of modes one and two result in the delivery of the effective dose.

Substances and Applications

The substances that can be used with delivery system 10, as well as the applications in which system 10 can be used, are very broad. As described in US Patent Application Publication 2009/0209945, there are numerous circumstances in which it can be desirable to deliver drugs or other agents in a tissue-specific manner, on an intermittent or continuous basis and using implantable drug delivery systems such as those described herein, to treat a particular condition. Disorders of the middle and inner ear can be treatable using the systems and methods described herein. Examples of middle and inner ear disorders include (but are not limited to) autoimmune inner ear disorder (AIED), Meniere's disease (idiopathic endolymphic hydrops), inner ear disorder associated with metabolic imbalances, inner ear disorder associated with infections, inner ear disorder associated with allergic or neurogenic factors, blast injury, noise-induced hearing loss, drug-induced hearing loss, tinnitus, presbycusis, barotrauma, otitis media (acute, chronic or serious), infectious mastoiditis, infectious myringitis, sensorineural hearing loss, conductive hearing loss, vestibular neuronitis, labyrinthitis, post-traumatic vertigo, perilymph fistula, cervical vertigo, ototoxicity, Mal de Debarquement Syndrome (MDDS), acoustic neuroma, migraine associated vertigo (MAV), benign paroxysmal positional vertigo (BPPV), eustachian tube dysfunction, cancers of the middle or inner ear, and infections (bacterial, viral or fungal) of the middle or inner ear. Degenerative ocular disorders can also be treatable using the systems and methods described herein. Examples of such degenerative ocular disorders include (but are not limited to) dry macular degeneration, glaucoma, macular edema secondary to vascular disorders, retinitis pigmentosa and wet macular degeneration. Similarly, inflammatory ocular diseases (including but not limited to birdshot retinopathy, diabetic retinopathy, Harada's and Vogt-Koyanagi-Harada syndrome, iritis, multifocal choroiditis and panuveitis, pars planitis, posterior scleritis, sarcoidosis, retinitis due to systemic lupus erythematosus, sympathetic ophthalmia, subretinal fibrosis, uveitis syndrome and white dot syndrome), ocular disorders associated with neovascularization (including but not limited to age-related macular degeneration, angioid streaks, choroiditis, diabetes-related iris neovascularization, diabetic retinopathy, idiopathic choroidal neovascularization, pathologic myopia, retinal detachment, retinal tumors, and sickle cell retinopathy), and ocular infections associated with the choroids, retina or cornea (including but not limited to cytomegalovirus retinitis, histoplasma retinochoroiditis, toxoplasma retinochoroiditis and tuberculous choroiditis) and ocular neoplastic diseases (including but not limited to abnormal tissue growth (in the retina, choroid, uvea, vitreous or cornea), choroidal melanoma, intraocular lymphoma (of the choroids, vitreous or retina), retinoblastoma, and vitreous seeding from retinoblastoma) can be treatable using the devices and methods described herein.

Further examples of conditions that can be treatable using the devices and methods described herein include, but are not limited to, the following: ocular, inner ear or other neural trauma; disorders of the auditory cortex; disorders of the inferior colliculus (by surface treatment or injection); neurological disorders of the brain on top of or below the dura; chronic pain; hyperactivity of the nervous system; migraines; Parkinson's disease; Alzheimer's disease; seizures; hearing related disorders in addition to those specified elsewhere herein; nervous disorders in addition to those specified elsewhere herein; ophthalmic disorders in addition to those specified elsewhere herein; ear, eye, brain disorders in addition to those specified elsewhere herein; cancers in addition to those specified elsewhere herein; bacterial, viral or fungal infections in addition to those specified elsewhere herein; endocrine, metabolic, or immune disorders in addition to those specified elsewhere herein; degenerative or inflammatory diseases in addition to those specified elsewhere herein; neoplastic diseases in addition to those specified elsewhere herein; conditions of the auditory, optic, or other sensory nerves; sensory disorders in additions to those specified elsewhere herein; conditions treatable by delivery of drug to the vicinity of the pituitary, adrenal, thymus, ovary, testis, or other gland; conditions treatable by delivery of drug to the vicinity of the heart, pancreas, liver, spleen or other organs; and conditions treatable by delivery of drug to specific regions of the brain or spinal cord.

The preceding identification of conditions is not intend to be exhaustive. Drug delivery systems and devices according to the embodiments described herein can be used to deliver one or more drugs to a particular target site so as to treat one or more of the conditions described above, as well as to treat other conditions. Drugs that can be delivered using the embodiments described herein include, but are not limited to, the following: antibiotics (including but are not limited to an aminoglycoside, an ansamycin, a carbacephem, a carbapenum, a cephalosporin, a macrolide, a monobactam, and a penicillin); anti-viral drugs (including but not limited to an antisense inhibitor, fomiversen, lamivudine, pleconaril, amantadine, and rimantadine); anti-inflammatory factors and agents (including but not limited to glucocorticoids, mineralocorticoids from adrenal cortical cells, dexamethasone, triamcinolone acetonide, hydrocortisone, sodium phosphate, methylprednisolone acetate, indomethacin, and naprosyn); neurologically active drugs (including but not limited to ketamine, caroverine, gacyclidine, memantine, lidocaine, traxoprodil, an NMDA receptor antagonist, a calcium channel blocker, a $GABA_A$ agonist, an $\alpha2\delta$ agonist, a cholinergic, and an anticholinergic); anti-cancer drugs (including but not limited to abarelix, aldesleukin, alemtuzamab, alitretinoin, allopurinol, altretamine, amifostine, anastrolzole, anti-hormones such as Arimidex, azacitidine, bevacuzimab, bleomycin, bortezomib, busulfan, capecitabine, carboplatin, carmustine, chlorambucil, cisplatin, cyclophosphamide, cyclosporine, darbepoetin, daunorubicin, docetaxel, doxorubicine, epirubicin, epoetin, etoposide, fluorouracil, gemicitabine, hydroxyurea, idarubicin, imatinib, interferon, letrozole, methotrexate, mitomycin C, oxaliplatin, paclitaxel, tamoxifen, taxol and taxol analogs, topothecan, vinblastine and related analogs, vincristine, and zoledronate); fungicides (including but not limited to azaconazole, a benzimidazole, captafol, diclobutrazol, etaconazole, kasugamycin, and metiram); anti-migraine medication (including but not limited to IMITREX); autonomic drugs (including but not limited to adrenergic agents, adrenergic blocking agents, anticholinergic agents, and skeletal muscle relaxants); anti-secretory molecules (including but not limited to proton pump inhibitors (e.g., pantoprazole, lansoprazole and rabprazole) and muscarinic antagonists (e.g., atropine and scopalomine)); central nervous system agents (including but not limited to analgesics, anti-convulsants, and antipyretics); hormones and synthetic hormones in addition to those described elsewhere herein; immunomodulating agents (including but not limited to etanercept, cyclosporine, FK506 and other immunosuppressant); neurotrophic factors and agents (factors and agents retarding cell degeneration, promoting cell sparing, or promoting new cell growth); angiogenesis inhibitors and factors (including but not limited to COX-2 selective inhibitors (e.g., CELEBREX), fumagillin (including analogs such as AGM-1470), and small molecules anti-angiogenic agents (e.g., thalidomide)); neuroprotective agents (agents capable of retarding, reducing or minimizing the death of neuronal cells) (including but not limited to N-methyl-D-aspartate (NMDA) antagonists, gacyclidine (GK11), and D-JNK-kinase inhibitors); and carbonic anhydrase inhibitors (including but not limited to acetazolamide (e.g., DIAMOX), methazolamide (e.g., NEPTAZANE), dorzolamide (e.g., TRUSOPT), and brinzolamide (e.g., AZOPT)).

In at least some embodiments, an implanted drug delivery system such as is described herein is used to deliver a drug (including but not limited to one or more of the drugs listed above) as a pure drug nanoparticle and/or microparticle suspension, as a suspension of nanoparticles and/or microparticles formed from drug formulated with binders and other ingredients to control release, or as some other type of nanoparticle- and/or microparticle-bound formulation. Nanoparticle- and/or microparticle-based delivery is advantageous in closed loop embodiments by allowing drug-containing particles to circulate within the closed loop as a solid suspended in the vehicle while delivering the desired therapeutic dose to the target tissue through the semi-permeable membrane or hollow fiber. Nanoparticle- and/or microparticle-bound delivery also offers the advantage of maintaining drug stability and avoiding loss of drug to polymeric components that can be encountered in a fluid pathway.

Many diseases and disorders are associated with one or more of angiogenesis, inflammation and degeneration. To treat these and other disorders, the embodiments disclosed herein can permit delivery of anti-angiogenic factors; anti-inflammatory factors; factors that retard cell degeneration, promote cell sparing, or promote cell growth; and combinations of the foregoing.

Diabetic retinopathy is characterized by angiogenesis. At least some embodiments contemplate treating diabetic retinopathy by implanting devices delivering one or more anti-angiogenic factors either intraocularly, preferably in the vitreous, or periocularly, preferably in the sub-Tenon's region. It can also be desirable to co-deliver one or more neurotrophic factors either intraocularly, periocularly, and/or intravitreally.

Uveitis involves inflammation. At least some embodiments contemplate treating uveitis by intraocular, vitreal or anterior chamber implantation of devices releasing one or more anti-inflammatory factors. Anti-inflammatory factors contemplated for use in at least some embodiments include, but are not limited to, glucocorticoids and mineralocorticoids (from adrenal cortical cells).

Retinitis pigmentosa is characterized by retinal degeneration. At least some embodiments contemplate treating retinitis pigmentosa by intraocular or vitreal placement of devices secreting one or more neurotrophic factors.

Age-related macular degeneration (wet and dry) involves both angiogenesis and retinal degeneration. Embodiments described herein can be used to deliver one or more neurotrophic factors intraocularly, preferably to the vitreous, and/or one or more anti-angiogenic factors intraocularly or periocularly, preferably periocularly, most preferably to the sub-Tenon's region.

Glaucoma is characterized by increased ocular pressure and loss of retinal ganglion cells. Treatments for glaucoma contemplated in at least some embodiments include delivery of one or more neuroprotective agents that protect cells from excitotoxic damage. Such agents include, but are not limited to, N-methyl-D-aspartate (NMDA) antagonists and neurotrophic factors. These agents can be delivered intraocularly, preferably intravitreally. Gacyclidine (GK11) is an NMDA antagonist and is believed to be useful in treating glaucoma and other diseases where neuroprotection would be helpful or where there are hyperactive neurons. Additional compounds with useful activity are D-JNK-kinase inhibitors.

Neuroprotective agents can be useful in the treatment of various disorders associated with neuronal cell death (e.g., following sound trauma, cochlear implant surgery, diabetic retinopathy, glaucoma, etc.). Examples of neuroprotective agents that can be used in at least some embodiments include, but are not limited to, apoptosis inhibitors, caspase inhibitors, neurotrophic factors and NMDA antagonists (such as gacyclidine and related analogs).

At least some embodiments can be useful for the treatment of ocular neovascularization, a condition associated with many ocular diseases and disorders and accounting for a majority of severe visual loss. For example, contemplated is treatment of retinal ischemia-associated ocular neovascularization, a major cause of blindness in diabetes and many other diseases; corneal neovascularization; and neovascularization associated with diabetic retinopathy, and possibly age-related macular degeneration.

One or more of the embodiments described herein can be used to deliver an anti-infective agent, such as an antibiotic, anti-viral agent or anti-fungal agent, for the treatment of an ocular infection. They can also be used to deliver a steroid, for example, hydrocortisone, dexamethasone sodium phosphate or methylprednisolone acetate, for the treatment of an inflammatory disease of the eye. One or more of the embodiments described herein can be used to deliver a chemotherapeutic or cytotoxic agent, for example, methotrexate, chlorambucil, or cyclosporine, for the treatment of a neoplasm. They can also be used to deliver an anti-inflammatory drug and/or a carbonic anhydrase inhibitor for the treatment of certain degenerative ocular disorders.

Chronic infections located in a specific tissue and suppressible by long-term local treatment without developing resistance (e.g., viral infections) can be treated using one or more of the embodiments described herein.

The above list of treating drug and treated condition examples are merely illustrative and do not exclude uses of one or more other drugs in the previous list of example drugs to treat a condition in the previous list of example conditions.

The devices and systems described herein can be configured for use in veterinary, diagnostic, laboratory, clinical research and development ("clinical R&D") or other types of environments, as well as use of such devices and/or systems in such environments.

While the specification describes particular embodiments of the systems, devices, and methods described herein, those of ordinary skill can devise variations to this subject matter without departing from the spirit and scope of the present disclosure. Thus, the claims are not intended to be limited to the embodiments shown, but are to be accorded the full scope consistent with the language of the claims, where reference to an element in the singular is not intended to mean "one and only one" unless specifically so stated, but rather "one or more." All structural and functional equivalents to the elements of the various embodiments described throughout this disclosure that are known or later come to be known to those or ordinary skill in the art are expressly incorporated herein by reference and are intended to be encompassed by the claims. Moreover, nothing disclosed herein is intended to be dedication to the public regardless of whether such disclosure is explicitly recited in the claims. No claim elements are to be construed under the provisions of 35 U.S.C. §112, sixth paragraph, unless the element is expressly recited using the phrase "means for" or, in the case of a method claim, the element is recited using the phrase "step for."

What is claimed is:

1. A method of manufacturing an implantable drug delivery system including an impedance pump, comprising:
   forming a first layer of a substrate with a reservoir and a pump chamber wall on which an activation element can be mounted, wherein the pump chamber wall is operable to be displaced to generate pumping forces;
   forming a second layer on the substrate having an elongate recess connected to a plurality of elongate channels;
   coupling the first layer to the second layer such that the pump chamber wall is positioned over the elongate recess, the elongate recess and the plurality of elongate channels are covered by the first layer, and the reservoir is in communication with at least one of the plurality of elongate channels; and
   coupling the activation element to the pump chamber wall.

2. The method of claim 1, further comprising inserting a medicament into the reservoir and sealing the reservoir.

3. The method of claim 1, wherein the plurality of elongate channels terminate in two or more openings in the sidewall of the substrate, the method further comprising:
   inserting drug perfusion tubing into the two or more openings; and
   overmolding the tubing to secure and seal the tubing to the substrate.

4. The method of claim 3, further comprising adding adhesive to further secure and seal the tubing to the substrate.

5. The method of claim 1, wherein the first and second layers are formed with a mold having features micromachined thereon.

* * * * *